US006890362B2

(12) United States Patent
Lang

(10) Patent No.: US 6,890,362 B2
(45) Date of Patent: May 10, 2005

(54) OXIDATION DYEING COMPOSITION FOR KERATINOUS FIBERS AND DYEING METHOD USING SAME

(75) Inventor: Gérard Lang, Saint-Prix (FR)

(73) Assignee: L'Oreal, S.A., Paris (FR)

( * ) Notice: Subject to any disclaimer, the term of this patent is extended or adjusted under 35 U.S.C. 154(b) by 122 days.

(21) Appl. No.: 09/959,704

(22) PCT Filed: Mar. 6, 2001

(86) PCT No.: PCT/FR01/00660

§ 371 (c)(1),
(2), (4) Date: Feb. 8, 2002

(87) PCT Pub. No.: WO01/66071

PCT Pub. Date: Sep. 13, 2001

(65) Prior Publication Data

US 2003/0009835 A1 Jan. 16, 2003

(30) Foreign Application Priority Data

Mar. 6, 2000 (FR) ............................................. 00 02857

(51) Int. Cl.⁷ ................................................ A61K 7/13
(52) U.S. Cl. ....................... 8/405; 8/406; 8/410; 8/411; 8/421
(58) Field of Search ............................ 8/405, 406, 410, 8/411, 421

(56) References Cited

U.S. PATENT DOCUMENTS

| | | | |
|---|---|---|---|
| 3,061,432 A | 10/1962 | Menzel et al. | ................... 96/55 |
| 3,227,554 A | 1/1966 | Barr et al. | ....................... 96/55 |
| 3,419,391 A | 12/1968 | Young | ......................... 96/56.5 |
| 3,725,067 A | 4/1973 | Bailey et al. | ................... 96/56.5 |
| 3,758,309 A | 9/1973 | Bailty et al. | .................... 96/136 |
| 3,926,631 A | 12/1975 | Arai et al. | ...................... 96/29 |
| 4,128,425 A | 12/1978 | Greenwald | ...................... 96/66 |
| 4,500,548 A | 2/1985 | Silva | ........................... 426/19 |
| 4,500,630 A | 2/1985 | Sato et al. | ................... 430/386 |
| 4,540,654 A | 9/1985 | Sato et al. | ................... 430/381 |
| 4,621,046 A | 11/1986 | Sato et al. | ................... 430/381 |
| 4,823,985 A | 4/1989 | Grollier et al. | ................. 222/1 |
| 5,256,526 A | 10/1993 | Suzuki et al. | ................ 430/389 |
| 5,279,619 A | 1/1994 | Cotteret et al. | ................ 8/406 |
| 5,344,464 A * | 9/1994 | Madrange et al. | ............. 8/410 |
| 5,364,414 A | 11/1994 | Lang et al. | ...................... 8/409 |
| 5,441,863 A | 8/1995 | Tang et al. | ................... 430/558 |
| 5,457,210 A | 10/1995 | Kim et al. | ................ 548/262.4 |
| 5,769,903 A * | 6/1998 | Audousset et al. | ............. 8/409 |
| 5,851,237 A * | 12/1998 | Anderson et al. | .............. 8/409 |
| 5,876,464 A | 3/1999 | Lim et al. | ....................... 8/409 |
| 5,976,195 A * | 11/1999 | de la Mettrie et al. | ......... 8/411 |
| 6,277,156 B1 | 8/2001 | Audousset | ..................... 8/407 |
| 6,613,313 B2 * | 9/2003 | Kimura | ..................... 424/70.1 |

FOREIGN PATENT DOCUMENTS

| | | |
|---|---|---|
| EP | 0 119 860 | 9/1984 |
| EP | 0 244 160 | 11/1987 |
| EP | 0 285 274 | 10/1988 |
| EP | 0 304 001 | 2/1989 |
| EP | 0 424 261 | 4/1991 |
| EP | 0 456 226 | 11/1991 |
| EP | 0 459 900 | 12/1991 |
| EP | 0 488 248 | 6/1992 |
| EP | 0 518 238 | 12/1992 |
| EP | 0 557 851 | 9/1993 |
| EP | 0 578 248 | 1/1994 |
| EP | 0 891 765 | 1/1999 |
| EP | 0 962 452 | 12/1999 |
| FR | 2 075 583 | 10/1971 |
| FR | 2 586 913 | 3/1987 |
| FR | 2 767 685 | 3/1999 |
| GB | 1 458 377 | 12/1976 |
| JP | 58 042045 | 3/1983 |
| JP | 59 099437 | 6/1984 |
| JP | 59 162548 | 9/1984 |
| JP | 59 171956 | 9/1984 |
| JP | 60 033552 | 2/1985 |
| JP | 60 043659 | 3/1985 |
| JP | 60 172982 | 9/1985 |
| JP | 60 190779 | 9/1985 |
| JP | 62 279337 | 12/1987 |
| JP | 6 236011 | 8/1994 |
| JP | 7 036159 | 2/1995 |
| JP | 7 084348 | 3/1995 |
| JP | 7 092632 | 4/1995 |
| JP | 7 098489 | 4/1995 |
| JP | 7 244361 | 9/1995 |
| JP | 7 325375 | 12/1995 |
| JP | 11 158046 | 6/1999 |
| JP | 11 158047 | 6/1999 |
| JP | 11 158048 | 6/1999 |

OTHER PUBLICATIONS

Co–Pending U.S. Appl. No. 09/959,702; filed Nov. 5, 2001, Gérard Lang, Oxidation Dyeing Composition for Keratinous Fibres and Dyeing Method Using Same.

Joseph Bailey, "Synthesis of 1 $H$–Pyrazolo [3,2-c]–s–Triazoles and Derived Azamethine Dyes", Journal of The Chemical Society, pp. 2047–2052, 1977.

Hans Beyer et al., "Über die Pyrazolbidung aus α–Chlor–acetessigester und Thiocarbohydrazid", Chemische Berichte, pp. 2550–2555, 1956.

R. Stollé, "Ueber die Ueberführung der secundären Säurehydrazide in Derivate des Furodiazols, Pyrrodiazols und Thiodiazols", Berichte Der Deutschen Chemischen Gesellschaft, pp. 797–798, 1899.

(Continued)

Primary Examiner—Margaret Einsmann
Assistant Examiner—Eisa Elhilo
(74) Attorney, Agent, or Firm—Finnegan, Henderson, Farabow, Garrett & Dunner, LLP

(57) ABSTRACT

The present invention relates to compositions comprising at least one oxidation base and at least one coupler, which is useful for the oxidation dyeing of keratinous fibers. The present invention also relates to a process for the oxidation dyeing of keratinous fibres, such as hair.

37 Claims, No Drawings

OTHER PUBLICATIONS

Mohamed Elnagdi et al., "Routes for the Synthesis of 3,5–Diaminopyrazoles, 2–Aminopyrazolo[1,5–a]pyrimidines and 5–Aminopyrazolo[1,5–a]pyrimidines", Journal Für Praktische Chemie, pp. 533–538, 1978.

E.J. Browne et al., "Triazoles. Part VII.★ Syntheses of Substituted 1,2,4–Triazoles", Journal of The Chemical Society, pp. 5149–5152, 1962.

Philip Magnus et al., "Synthesis of Helical Poly–β–pyrroles. Multiple Atropisomerism Resulting in Helical Enantiomorphic Conformations", Journal of the American Chemical Society, pp. 2465–2468, 1990.

Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of The American Chemical Society, pp. 2711–2717, 1987.

Dr. H. Gold, "Die Reaktion von Cyanurcholorid mit Dimethylformamid", Angewandte Chemie, pp. 956–959, 1960.

H. Koopman, :"Investigations on Herbicides IV, The synthesis of 2,6–dischlorobenzonitrile", Recueil, pp. 1075–1083, 1960.

Lidia Wyzgowska, et al., "O ReakcjachTrikarboetoksymetanu", Acta Poloniae Pharmaceutica, pp, 83–88, 1981.

E. Hanning et al., "Kurze Orginalmitteilungen", Die Pharmazie, p. 231, 1980.

Mohamed Elnagdi et al., "Studies on 3,5–pyrazolidinediones. IV. Addition of 4–Arylazo–3,5–pyrazolidinediones to Ethyl Acrylate", Bulletin of the Chemical Society of Japan, vol. 46, 1973. pp. 1831–1833.

Giuliana Cardillo et al., "Sulle 1,2–difenil–3,5–dichetopirazolidine", Gazzetta Chimica Italiana, vol. 96, 1966, pp. 973–985.

Mohamed Ali et al., "Reactions with Thiazolo[3,2–b]–s–triazol–3(2H)–ones", Journal Für Praktische Chemie, pp. 12–18, 1975.

Eser Ilhan, et al., "Synthese von 6–Benzyliden–2–(α, α–diphenyl–α–hydroxyacetyl)–thiazolo [3,2–b]–s–trialzol–5–onen als potentiell biologisch wirksame Stroffe", Archiv der Pharmazie, pp. 825–826, 1994.

P.M. Kochergin et al., "Imidazo [5,1–b] Thiazo [5,1–b]–Thiazolines, and Imidazo [5,1–b] Thiazolid–3–Ones", Chemistry of Heterocyclic Compounds, pp. 66–67, 1965.

Henryk Foks et al., "Synthesis and Biological Activity of Thiazolo–1,2,4–Triazoles", Acta Poloniae Pharmaceutica—Drug Research, pp. 415–420, 1995.

English language Derwent Abstract of JP 6 236011, Aug. 23, 1994.

English language Derwent Abstract of JP 7 036159, Feb. 7, 1995.

English language Derwent Abstract of JP 7 084348, Mar. 31, 1995.

English language Derwent Abstract of JP 7,092632, Apr. 7, 1995.

English language Derwent Abstract of JP 7 098489, Apr. 11, 1995.

English language Derwent Abstract of JP 7 244361, Sep. 19, 1995.

English language Derwent Abstract of JP 7 325375, Dec. 12, 1995.

English language Derwent Abstract of JP 11 158046, Jun. 15, 1999.

English language Derwent Abstract of JP 11 158047, Jun. 15, 1999.

English language Derwent Abstract of JP 11 158048, Jun. 15, 1999.

English language Derwent Abstract of JP 58 042045, Mar. 11, 1983.

English language Derwent Abstract of JP 59 099437, Jun. 8, 1984.

English language Derwent Abstract of JP 60 033552, Feb. 20, 1985.

English language Derwent Abstract of JP 60 043659, Mar. 8, 1985.

English language Derwent Abstract of JP 60 190779, Sep. 28, 1985.

English language Derwent Abstract of JP 62 279337, Dec. 4, 1987.

* cited by examiner

OXIDATION DYEING COMPOSITION FOR KERATINOUS FIBERS AND DYEING METHOD USING SAME

CROSS-REFERENCE TO RELATED APPLICATIONS

This application is a national stage entry under 35 U.S.C. § 371 from International Application No. PCT/FR01/00660, filed Mar. 6, 2001, which claims priority to Application No. 00/02857, filed Mar. 6, 2000, in France.

A subject-matter of the invention is a composition for the oxidation dyeing of keratinous fibres and in particular of human keratinous fibres, such as the hair, comprising, in a medium appropriate for dyeing, at least one oxidation base chosen from certain substituted para-phenylenediamine derivatives and their addition salts with an acid and at least one selected coupler, and the dyeing process employing this composition.

It is known to dye keratinous fibres and in particular human hair with dyeing compositions comprising oxidation dye precursors, in particular ortho- or para-phenylenediamines, ortho- or para-aminophenols or heterocyclic bases, generally known as oxidation bases. Oxidation dye precursors or oxidation bases are colourless or weakly coloured compounds which, in combination with oxidizing substances, can give rise by an oxidative coupling process to coloured and colouring compounds.

It is also known that the shades obtained with these oxidation bases can be varied by combining them with couplers or colouring modifiers, the latter being chosen in particular from aromatic meta-diamines, meta-aminophenols, meta-diphenols and certain heterocyclic compounds.

The variety of the molecules employed as oxidation bases and couplers makes it possible to obtain a rich palette of colours.

The so-called "permanent" colouring obtained by virtue of these oxidation dyes has, however, to satisfy a certain number of requirements. Thus, it must make it possible to obtain shades with a desired intensity and behave well in the face of external agents (light, bad weather, washing, permanent waving, perspiration or rubbing).

The dyes must also make it possible to cover white hair and, finally, be as unselective as possible, that is to say make it possible to obtain the least possible differences in colouring along the same keratinous fibre, this being because the latter can be sensitized (i.e. damaged) to a varying degree between its tip and its root.

Provision has already been made, in particular in Patent Applications JP-11158046, JP-11158047 and JP-11158048, for compositions for the oxidation dyeing of keratinous fibres comprising, as oxidation dye precursors, certain substituted para-phenylenediamine derivatives. However, the colourings obtained on employing these compositions are not always powerful enough, chromatic enough or sufficiently resistant to the various attacks which the hair may be subjected to.

In point of fact, the Applicant Company has now just discovered that it is possible to obtain novel dyes, which dyes are capable of resulting in colourings with varied shades which are chromatic, powerful, attractive, not very selective and highly resistant to the various attacks which the fibres may be subjected to, by combining at least one oxidation base chosen from certain para-phenylenediamine derivatives of formula (I) defined below and their addition salts with an acid and at least one suitably selected coupler.

This discovery forms the basis of the present invention.

A first subject-matter of the invention is thus a composition for the oxidation dyeing of keratinous fibres and in particular of human keratinous fibres, such as the hair, characterized in that it comprises, in a medium appropriate for dyeing:

at least one oxidation base chosen from substituted para-phenylenediamine derivatives of following formula (I) and their addition salts with an acid:

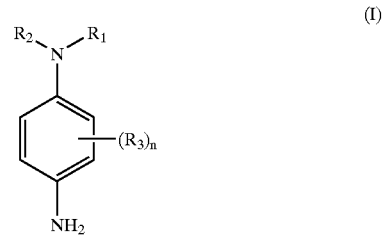

in which:

$R_1$ and $R_2$ can take one of the following meanings i) to v):
  i) $R_1$ and $R_2$ simultaneously represent a —(CH$_2$)$_2$CHOHCH$_2$OH radical; or
  ii) $R_1$ represents a —CH$_2$(CHOH)$_4$CH$_2$OH radical and $R_2$ represents a hydrogen atom, an alkyl or aryl radical or a heterocycle; or
  iii) $R_1$ represents an alkyl or aryl radical or a heterocycle and $R_2$ represents an alkylene radical —(CH$_2$)$_m$— in which m is an integer equal to 2 or to 3, the said alkylene radical forming a ring in conjunction with the nitrogen atom, the carbon atom of the benzene ring carrying the nitrogen atom and one of the two carbon atoms of the benzene ring which are adjacent to it, it being understood that, when $R_1$ is an alkyl or aryl radical, then either $R_1$ or the said alkylene radical is substituted by a radical comprising at least one nitrogen, oxygen or sulphur atom;
  iv) $R_1$ represents a —(CH$_2$CH$_2$O)$_p$R$_4$ radical in which p is an integer between 2 and 8 inclusive and $R_4$ and $R_2$, which are identical or different, represent a hydrogen atom, an alkyl or aryl radical or a heterocycle;
  v) $R_1$ and $R_2$ form, in conjunction with the nitrogen atom to which they are attached, a saturated 5-, 6- or 7-membered heterocycle, the said heterocycle being substituted by at least one radical comprising at least one carbon, nitrogen, oxygen or sulphur atom;

$R_3$ represents a halogen atom, an alkyl or aryl radical, a heterocycle, a heterocycle connected to the benzene ring of the formula (I) via an ether or sulphide bond, or a cyano, nitro, hydroxyl, carboxyl, sulpho, alkoxy, aryloxy, cyanoamino, amino, anilino, ureido, sulphamoyl, mono- or dialkyl-sulphamylamino, alkylthio, arylthio, alkoxycarbonylamino, sulphonamido, carbamyl, mono- or dialkylcarbamylsulphamyl, alkylsulphonyl, alkoxycarbonyl, azo, acyloxy, carbamyloxy, mono- or dialkyl-carbamyloxy, silyl, silyloxy, aryloxycarbonylamino, imido, sulphinyl, phosphonyl, aryloxycarbonyl, acyl or mercapto radical; the said alkyl radicals comprising from 1 to 25 carbon atoms and being able to be linear, branched or cyclic and to be substituted by one or more radicals and then to represent a mono- or polyhydroxyalkyl, alkoxyalkyl, aminoalkyl, optionally substituted on the nitrogen atom, carboxyalkyl, alkylcarboxyalkyl, thioalkyl, alkylthioalkyl, cyanoalkyl, trifluoroalkyl, sulphoalkyl, phosphoalkyl or haloalkyl radical; the said alkoxy radicals comprising from 1 to 25 carbon atoms and being able to be linear, branched or cyclic; the said aryl radicals comprising from 6 to 26 carbon atoms and being able to be substituted by one or more radicals chosen from alkyl, substituted alkyl or alkoxy radicals; the heterocycles being mono- or polycyclic, each ring comprising 3, 4, 5 or 6 ring members and being able to comprise one or more heteroatoms, it being understood that, in the case of polycyclic heterocycles, at least one of the rings comprises at least one heteroatom such as N, O or S;

n is an integer between 0 and 4; it being understood that, when n is greater than 1, then the $R_3$ radicals can be identical or different and can form, with one another, a saturated or unsaturated 3-, 4-, 5- or 6-membered ring; with the proviso that:

1) when $R_1$ and $R_2$ have the meanings defined in point v), then the compounds of formula (I) do not comprise more than 3 hydroxyl radicals;
2) when $R_1$ and $R_2$ have the meanings defined in point v) and when $R_1$ and $R_2$ form a pyrrolidine ring substituted by a carbamoyl radical on the carbon in the position a to the nitrogen atom to which they are attached, then n is other than 0; or else the pyrrolidine ring carries at least two substituents;
3) when $R_1$ and $R_2$ have the meanings defined in point v) and when $R_1$ and $R_2$ form a pyrrolidine ring substituted by a hydroxymethyl radical on the carbon situated in the a position with respect to the nitrogen atom to which they are attached and when n=0 or 1, then either the said ring carries at least two additional substituents or the said ring comprises only one second substituent other than a hydroxyl radical on the carbon situated in the β position with respect to the nitrogen atom and with respect to the carbon carrying the said hydroxymethyl substituent; or else, when $R_1$ and $R_2$ have the meanings defined in point v) and $R_1$ and $R_2$ form a pyrrolidine ring substituted by a hydroxymethyl radical on the carbon situated in the α position with respect to the nitrogen atom to which they are attached and when n=1, then $R_3$ is other than an alkyl or mono- or polyhydroxyalkyl radical;
4) when $R_1$ and $R_2$ have the meanings defined in point iii), the compounds of formula (I) must fulfil at least one of the following four conditions:
   a) whatever the value of n, the alkylene ring formed by the $R_2$ radical comprises a substituent in addition to the $R_1$ radical; or
   b) n is greater than 1; or
   c) when n is equal to 1, then $R_3$ represents an aryl radical or a heterocycle; or
   d) when n is equal to 0 or to 1, then $R_1$ represents an aryl radical, a heterocycle or a substituted alkyl radical other than a monohydroxyalkyl radical;
5) when $R_1$ and $R_2$ have the meanings defined in point v), the $R_1$ and $R_2$ groups form a heterocycle other than the piperazines and the diazacycloheptanes;

at least one coupler chosen from heterocyclic couplers, substituted meta-diphenols, substituted meta-phenylenediamines, naphthols and acylated naphthols, and the meta-aminophenols of following formula (II) and their addition salts with an acid:

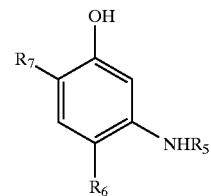

(II)

in which:
$R_5$ represents a hydrogen atom or a $C_1$–$C_4$ alkyl, $C_1$–$C_4$ monohydroxyalkyl or $C_2$–$C_4$ polyhydroxyalkyl radical,
$R_6$ represents a hydrogen atom, a $C_1$–$C_4$ alkyl or $C_1$–$C_4$ alkoxy radical or a halogen atom chosen from chlorine, bromine or fluorine,
$R_7$ represents a hydrogen atom or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical;

with the proviso that, when $R_7$ denotes a methyl radical and $R_6$ denotes a hydrogen atom, then $R_5$ does not denote a hydrogen atom.

The dyeing composition in accordance with the invention results in colourings in varied shades which are chromatic, powerful and attractive and which exhibit low selectivity and excellent properties of resistance both with regard to atmospheric agents, such as light and bad weather, and with regard to perspiration and the various treatments which the hair may be subjected to.

According to a specific embodiment, the oxidation base is chosen from substituted para-phenylenediamine derivatives of following formula (I) and their addition salts with an acid:

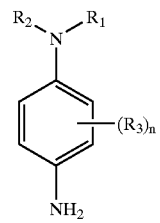

(I)

in which:
$R_1$ and $R_2$ can take one of the following meanings i) to v):
i) $R_1$ and $R_2$ simultaneously represent a —$(CH_2)_2$CHOHCH$_2$OH radical; or
ii) $R_1$ represents a —$CH_2(CHOH)_4CH_2OH$ and $R_2$ represents a hydrogen atom or an alkyl radical; or
iv) $R_1$ represents a —$(CH_2CH_2O)_pR_4$ radical in which p is an integer between 2 and 8 inclusive and $R_4$ and $R_2$, which are identical or different, represent a hydrogen atom or an alkyl radical;
v) $R_1$ and $R_2$ form, in conjunction with a nitrogen atom to which they are attached, a saturated 5-, 6- or 7-membered heterocycle, the said heterocycle being substituted by at least one radical comprising at least one carbon or a nitrogen or oxygen atom not situated in the meta position with respect to the nitrogen atom of the heterocycle;

—$R_3$ represents a halogen atom, an alkyl or aryl radical, or a heterocycle;

n is an integer equal to 0, 1 or 2.

According to one embodiment of the invention, the $R_1$ and $R_2$ groups form a heterocycle comprising a single heteroatom, nitrogen, for example a pyrrolidine heterocycle.

Mention may very particularly be made, among the substituted para-phenylenediamine derivatives of above formula (I), of 1-N,N-bis(3',4'-dihydroxybutyl)-para-phenylenediamine, 1-N,N-bis(3',4'-dihydroxybutyl)-3-methyl-para-phenylenediamine, 1-N,N-bis(3',4'-dihydroxybutyl)-3-ethyl-para-phenylenediamine, 1-N,N-bis(3',4'-dihydroxybutyl)-3-propyl-para-phenylenediamine, 1-N,N-bis(3',4'-dihydroxybutyl)-3-methoxy-para-phenylenediamine, 1-N,N-bis(3',4'-dihydroxybutyl)-3-ethoxy-para-phenylenediamine, 1-N,N-bis(3',4'-dihydroxybutyl)-3-propyloxy-para-phenylenediamine, 1-N,N-bis(3',4'-dihydroxybutyl)-3-hexyloxy-para-phenylenediamine, 1-N,N-bis(3',4'-dihydroxybutyl)-3-(1"-N-3",5"-dimethylpyrazolyl-para-phenylenediamine, 1-N,N-bis(3',4'-dihydroxybutyl)-3-ureido-para-phenylenediamine, 1-N,N-bis(3',4'-dihydroxybutyl)-3-(1",3",3"-trimethylureido)-para-phenylene-diamine, 1-N,N-bis(3',4'-dihydroxybutyl)-3-dimethylamino-para-phenylenediamine, 1-N,N-bis(3',4'-dihydroxybutyl)-3-methylthio-para-phenylenediamine, 1-N,N-bis(3',4'-dihydroxybutyl)-3-ethylthio-para-phenylenediamine, 1-N,N-bis(3',4'-dihydroxybutyl)-3-mercapto-para-phenylenediamine, 1-N,N-bis(3',4'-dihydroxybutyl)-3-n-butylthio-para-phenylenediamine, 1-N,N-bis(3',4'-dihydroxybutyl)-3-n-octylthio-para-phenylenediamine, 1-N,N-bis(3',4'-dihydrbxybutyl)-3-mercaptoethyl-para-phenylenediamine, 1-N,N-bis(3',4'-dihydroxybutyl)-3-mercaptoethylthio-para-phenylenediamine, 1-N,N-bis(3',4'-dihydroxybutyl)-3-β-hydroxyethylthio-para-phenylenediamine, 1-N-(2',3',4',5',6'-pentahydroxyhexyl)-para-phenylenediamine, 1-N-(2',3',4',5',6'-pentahydroxyhexyl)-3-methyl-para-phenylenediamine, 1-N-(2',3',4',5',6'-pentahydroxyhexyl)-3-isopropyl-para-phenylenediamine, 1-N-(2',3',4',5',6'-pentahydroxyhexyl)-3-methoxy-para-phenylenediamine, 1-N-(2',3',4',5',6'-pentahydroxyhexyl)-1-N-(4"-N"-methylpiperidyl)-3-ethoxy-para-phenylenediamine, 1-N-(2',3',4',5',6'-pentahydroxyhexyl)-3-isopropyloxy-para-phenylenediamine, 1-N-(2',3',4',5',6'-pentahydroxyhexyl)-3-dimethylamino-para-phenylenediamine, 1-N-(2',3',4',5',6'-pentahydroxyhexyl)-3-methylthio-para-phenylenediamine, 1-N-(2',3',4',5',6'-pentahydroxyhexyl)-3-mercapto-para-phenylenediamine, 1-N-(hexyl)-1-N-(2',3',4',5',6'-pentahydroxyhexyl)-3-iospropyl-para-phenylenediamine, 1-N-(methyl)-1-N-(2',3',4',5',6'-pentahydroxyhexyl)-3-isooctyloxy-para-phenylenediamine, 1-N-(methyl)-1-N-(2',3',4',5',6'-pentahydroxyhexyl)-3-isopropyloxy-para-phenylenediamine, 1-N-(methyl)-1-N-(2',3',4',5',6'-pentahydroxyhexyl)-3-methyl-para-phenylenediamine, 1-N-(methyl)-1-N-(2',3',4',5',6'-pentahydroxyhexyl)-3-ethyl-para-phenylenediamine, 1-N-(methyl)-1-N-(2',3',4',5',6'-pentahydroxyhexyl)-3-hydroxyethyloxy-para-phenylenediamine, 1-N-(methyl)-1-N-(2',3',4',5',6'-pentahydroxyhexyl)-3-mercaptoethyloxy-para-phenylenediamine, 1-N-(methyl)-1-N-(2',3',4',5',6'-pentahydroxyhexyl)-para-phenylenediamine, 1-N-(phenyl)-1-N-(2',3',4',5',6'-pentahydroxyhexyl)-3-ethyloxy-para-phenylenediamine, 1-N-(4"-N-methylpiperidyl)-1-N-(2',3',4',5',6'-pentahydroxyhexyl)-3-ethyloxy-para-phenylenediamine, 4-N-(methyl)-4-N-(2',3',4',5',6'-pentahydroxyhexyl)amino-7-amino-1-methylindole, 1-N-(hydroxyethyloxyethyl)-1-N-(2',3',4',5',6'-pentahydroxyhexyl)-3-ethyl-para-phenylenediamine and their addition salts with an acid.

The oxidation base is preferably chosen from 1-N,N-bis(3',4'-dihydroxybutyl)-para-phenylenediamine, 1-N,N-bis(3',4'-dihydroxybutyl)-3-methyl-para-phenylenediamine, 1-N,N,-bis(3',4'-dihydroxybutyl)-3-ethyl-para-phenylenediamine, 1-N,N,-bis(3',4'-dihydroxybutyl)-3-propyl-para-phenylenediamine, 1-N-(2',3',4',5',6'-pentahydroxyhexyl)-para-phenylene-diamine, 1-N-(2',3',4',5',6'-pentahydroxyhexyl)-3-methyl-para-phenylenediamine, 1-N-(2',3',4',5',6'-pentahydroxyhexyl)-3-isopropyl-para-phenylenediamine, 1-N-(hexyl)-1-N-(2',3',4',5',6'-pentahydroxyhexyl)-3-isopropyl-para-phenylenediamine, 1-N-(methyl)-1-N-(2',3',4',5',6'-pentahydroxyhexyl)-3-methyl-para-phenylenediamine, 1-N-(methyl)-1-N-(2',3',4',5',6'-pentahydroxyhexyl)-3-ethyl-para-phenylenediamine, 1-N-(methyl)-1-N-(2',3',4',5',6'-pentahydroxyhexyl)-para-phenylenediamine, 1-N-(hydroxyethyloxyethyl)-1-N-(2',3',4',5',6'-pentahydroxyhexyl)-3-ethyl-para-phenylenediamine and their addition salts with an acid.

Mention may also very particularly be made of 1-N-(3',4'-dihydroxybutyl)-5-aminoindoline, 1-(2'-hydroxyethyl)-2-methyl-5-aminoindoline, 1-methyl-2-hydroxymethyl-5-aminoindoline, 6-methyl-2-hydroxy-ethyl-5-aminoindoline, 2-hydroxyethyloxyethyl-5-aminoindoline, 2-hydroxyethyloxyethyloxyethyloxyethyl-5-aminoindoline, 2-hydroxyethyloxyethyloxyethyloxyethyloxyethyloxyethyl-6-isopropyl-5-aminoindoline, 2-hydroxyethyl-3-methyl-5-aminoindoline, 2-hydroxyethyloxyethyloxyethyl)-5-aminoindoline, 1-carboxymethyl-2,3,3-trimethyl-5-aminoindoline, 1-methylsulphonamidoethyl-3-methyl-5-aminoindoline, 1-ureidoethyl-6-methoxy-5-aminoindoline, 1-(2',3',4',5',6'-pentahydroxyhexyl)-5-aminoindoline, 1-N-(2'-mercaptoethyl)-5-aminoindoline, the dimethyl ester 6-amino-1-methyl-1,2,3,4-tetrahydrofuro[2,3,h]quinoline-4-methyl ester of phosphoric acid, 6-amino-1,2,2-trimethyl-4-trimethylsilanyloxy-1,2,3,4-tetrahydroquinoline, 6-amino-1-hexyl-2,2,7-trimethyl-4-mercaptomethyl-1,2,3,4-tetrahydroquinoline, 6-amino-1-(3',4'-dihydroxybutyl)-2,2,3-trimethyl-1,2,3,4-tetrahydroquinoline, 6-amino-1-(ethoxyethoxyethoxy-3',4'-dihydroxybutyl)-2,2,3,7-tetramethyl-1,2,3,4-tetrahydroquinoline, 6-amino-1-(hydroxyethyloxyethyloxyethyloxyethyl)-2,2,3-trimethyl-1,2,3,4-tetrahydroquinoline, 6-amino-1-(hydroxyethyloxyethyl)-2,2,3-trimethyl-1,2,3,4-tetrahydroquinoline, 6-amino-1-(ethylbis(hydroxyethyloxyethyloxyethyloxyethyl))-2,2,3,7-tetramethyl-1,2,3,4-tetrahydroquinoline, 1-(carboxymethyl)-2,2,3,7-tetramethyl-1,2,3,4-tetrahydroquinoline, 1-(hydroxypropyl)-2,2,3-trimethyl-7-methoxy-1,2,3,4-tetrahydroquinoline, 6-amino-1-(hydroxyethyloxyethyloxyethyl)-2,2,3-trimethyl-7-isopropyl-1,2,3,4-tetrahydroquinoline, 6-amino-1-(hydroxyethyloxyethyloxyethyloxyethyloxyethyloxyethyl)-2,2,3-trimethyl-7-isopropyl-1,2,3,4-tetrahydroquinoline, 6-amino-1-(hydroxyethyloxyethylxyethyloxyethyloxyethyloxyethyloxyethyl)-2,2,3-trimethyl-1,2,3,4-tetrahydroquinoline, 6-amino-1-(mercaptoethyl)-1,2,3,4-tetrahydroquinoline, 6-amino-1-(3',4'-dihydroxybutyl)-2,2,3-trimethyl-7-isopropyl-1,2,3,4-tetrahydroquinoline, 6-amino-1-(3',4'-dihydroxybutyl)-2,2,7-trimethyl-4-hydroxymethyl-1,2,3,4-tetrahydroquinoline, 6-amino-1-(3',4'-dihydroxybutyl)-2,2-dimethyl-4-hydroxymethyl-7-isopropyl-1,2,3,4-tetrahydroquinoline, 6-amino-1-(3-hydroxypropyl)-2,2-dimethyl-4-hydroxymethyl-7-isopropyl-1,2,3,4-tetrahydroquinoline, 6-amino-1-(hydroxyethyloxyethyloxyethyloxyethyloxyethyloxyethyloxyethyloxyethyl)-2,2-dimethyl-4-hydroxymethyl-7-isopropyl-1,2,3,4-tetrahydroquinoline, 6-amino-1-(hydroxyethyloxyethyloxyethyloxyethyl)-2,2-dimethyl-4-hydroxymethyl-7-isopropyl-1,2,3,4-tetrahydroquinoline, 6-amino-1-(hydroxyethyloxyethyloxyethyloxyethyloxyethyl)-2,2-dimethyl-7-isopropyl-1,2,3,4-tetrahydroquinoline, 6-amino-1-(hydroxyethyloxyethyloxyethyloxyethyloxyethyl)-2,2-dimethyl-7-isopropyl-1,2,3,4-tetrahydroquinoline, 6-amino-1-(hydroxyethyloxyethyl)-2,2-dimethyl-1,2,3,4-tetrahydroquinoline, 6-amino-1,2,2,4,7-pentamethyl-3-hydroxy-1,2,3,4-tetrahydroquinoline, 6-amino-1-(3'-hydroxypropyl)-4-(hydroxyethyloxyethyloxyethyloxyethyl)-2,2-dimethyl-7-isopropyl-1,2,3,4-tetrahydroquinoline, 6-amino-1-(hydroxyethyloxyethyloxyethyloxyethyl)-4,4-dimethyl-1,2,3,4-tetrahydroquinoline, 6-amino-1-(3',4'-dihydroxybutyl)-2,2-dimethyl-7-isopropyl-1,2,3,4-tetrahydroquinoline, 6-amino-1-(hydroxyethyloxyethyloxyethyloxyethyl)-4-(hydroxyethyloxyethyloxyethyloxyethyl)-2,2,7-trimethyl-1,2,3,4-tetrahydroquinoline, 6-amino-1-(hydroxyethyloxyethyloxyethyloxyethyl)-2,2-dimethyl-7-isopropyl-1,2,3,4-tetrahydroquinoline, 6-amino-1-(2',3',4',5',6'-pentahydroxyhexyl)-2,2,4-trimethyl-7-isopropyl-1,2,3,4-tetrahydroquinoline, 6-amino-1-(mercaptoethyl)-2,2,4-trimethyl-7-(2',3'-dihydroxypropyloxy)-1,2,3,4-tetrahydroquinoline, 6-amino-1-(3',4'-dihydroxybutyl)-2,2,7-trimethyl-3-mercaptomethyl-1,2,3,4-tetrahydroquinoline, 6-amino-1-(ureidoethyl)-2,2,4-trimethyl-1,2,3,4-tetrahydroquinoline, 6-amino-2,2-dimethyl-7-chloro-1,2,3,4-tetrahydroquinoline-1-propylsulphonic acid, 6-amino-1-(4'-pyridinyl)-2,2,7-trimethyl-1,2,3,4-tetrahydroquinoline, 6-amino-1-(3',4'-dihydroxybutyl)-2,2,4,7-tetramethyl-1,2,3,4-tetrahydroquinoline, 6-amino-1,7-diisopropyl-2,2-dimethyl-4-trimethylsilanyloxy-1,2,3,4-tetrahydroquinoline, 6-amino-1,2,2,4-tetramethyl-3-hydroxy-1,2,3,4-tetrahydroquinoline, 6-amino-1-bromo-2,2-dimethyl-4-mercapto-7-isopropyloxy-1,2,3,4-tetrahydroquinoline, and their addition salts with an acid.

Mention may also very particularly be made of 1-(4'-amino-3'-isopropyloxyphenyl)-2,6-dimethylpyrrolidine, 1-(4'-amino-3'-methylphenyl)-3-(hydroxyethyloxy)pyrrolidine, 1-(4'-amino-3'-methylphenyl)-4-hydroxy-2-methylpyrrolidine, 1-(4'-amino-3'-methylphenyl)-3-(methylsulphonamido)pyrrolidine, 1-(4'-amino-3'-phenoxyphenyl)-3-(methylsulphon-amido)pyrrolidine, 3-n-butylpyrrolidine-1-(4'-amino-3'-phenylsulphonic acid), 1-(4'-amino-3'-acetylamino-phenyl)-3-(hydroxymethyl)pyrrolidine, 7-amino-4-(2'-methyl)-pyrrolydinyl-benzofuran, 1-(4'-amino-phenyl)-2-(4"-aminophenoxymethyl)piperidine, 1-(4'-amino-3'-acetylphenyl)-4-hydroxypiperidine, 1-(4'-aminophenyl)-2-(hydroxyethyl)piperidine, 1-(4'-amino-3'-methoxyphenyl)-2,6-di(hydroxymethyl)piperidine, 1-(4'-amino-3'-isopropyloxyphenyl)-2,6-dimethylpiperidine, 1-(4'-amino-3'-isopropylphenyl)-2-(hydroxymethyl)piperidine, 1-(4'-amino-3'-isopropyloxyphenyl)-2-(hydroxymethyl)piperidine, 1-(4'-amino-3'-aminophenyl)-2-(hydroxymethyl)piperidine, 1-(4'-amino-3'-dimethylaminophenyl)-2-(mercaptoethyloxyethyl)piperidine, 1-(4'-amino-3'-(2''',4'''-dichloro)anilinophenyl)-4-methylpiperidine, 1-(4'-aminophenyl)-4-methylpiperidine, 1-(4'-aminophenyl)-2,7-dimethylazacycloheptane, 1-(4'-amino-3'-methylphenyl)-2-methylazacycloheptane, 1-(4!-amino-3'-ureidophenyl)-3-hydroxyazacycloheptane, 1-(4'-amino-3'-sulphamoylaminophenyl)-2,7-dimethylazacycloheptane, 1-(4'-amino-3'-methylthiophenyl)-2,7-dimethylazacycloheptane, 1-N-(4'-hydroxybutyl)-1-N-(hydroxyethyloxyethyloxyethyl)-3-isopropyl-para-phenylenediamine, 1-N-methyl-1-N-(hydroxyethyloxyethyloxyethyl)-para-phenylenediamine, 1-N-phenyl-1-N-(hydroxyethyloxyethyl)-para-phenylenediamine, 1-N-benzyl-1-N-(hydroxyethyloxyethyloxyethyloxyethyl)-3-trimethylsilyl-para-phenylenediamine, 1-N-methyl-1-N-(hydroxyethyloxyethyloxyethyloxyethyloxyethyloxyethyl)-3-trimethylsilyloxy-para-phenylenediamine, 1-N-ethyl-1-N-(methoxyethyloxyethyloxyethyloxyethyl)-3-phenoxycarbonylamino-para-phenylenediamine, 1-N-methyl-1-N-(methoxyethyloxyethyloxyethyl)-3-(2',5'-dioxopyrrolidinyl)-para-phenylenediamine, 1-N-ethyl-1-N-(hydroxyethyloxyethyloxyethyl)-3-(4'-pyridinylthio)-para-phenylenediamine, 1-N-propyl-1-N-(hydroxyethyloxyethyloxyethyl)-3-sulphinyl-para-phenylenediamine, 1-N-methyl-1-N-(hydroxyethyloxyethyl)-3-phenoxycarbonyl-para-phenylenediamine, 1-N,N-bis(hydroxyethyloxyethyloxyethyloxyethyl)-para-phenylenediamine, 1-N,N-bis(methoxyethyloxyethyloxyethyloxyethyl)-3-isopropyl-oxy-para-phenylenediamine, 1-N,N-bis(hydroxyethyloxyethyloxyethyl)-3-isopropyloxy-para-phenylenediamine, 1-N,N-bis(hydroxyethyloxyethyloxyethyloxyethyl)-3-isopropyl-para-phenylenediamine, 1-N,N-bis(hydroxyethyloxyethyloxyethyloxyethyl)-3-isopropyl-para-phenylenediamine, 1-N,N-bis(methoxyethyloxyethyloxyethyloxyethyloxyethyloxyethyloxyethyl)-3-methoxy-para-phenylenediamine, 1-N,N-bis(hydroxyethyloxyethyloxyethyloxyethyloxyethyloxyethyloxyethyl)-3-methyl-para-phenylenediamine, 1-N,N-bis(hydroxyethyloxyethyloxyethyloxyethyl)-3-isopropyloxy-para-phenylenediamine, 1-N,N-bis(hydroxyethyloxyethyl)-3-mercaptoethyl-para-phenylenediamine, 1-N,N-bis(benzyloxyethyloxyethyloxyethyl)-3-isopropyl-para-phenylenediamine and their addition salts with an acid.

The oxidation base is preferably chosen from 1-(4'-amino-3'-methylphenyl)-3-(hydroxyethyloxy)pyrrolidine, 1-(4'-amino-3'-methylphenyl)-4-hydroxy-2-methylpyrrolidine, 1-(4'-amino-3'-methylphenyl)-3-(methylsulphonamido)pyrrolidine, 1-(4'-amino-3'-phenoxyphenyl)-3-(methylsulphonamido)pyrrolidine, 1-(4'-aminophenyl)-2-(4"-aminophenoxymethyl)piperidine, 1-(4'-aminophenyl)-2-(hydroxyethyl)piperidine, 1-(4'-amino-3'-isopropylphenyl)-2-(hydroxymethyl)piperidine, 1-(4'-aminophenyl)-4-methylpiperidine, 1-(4'-aminophenyl)-2,7-dimethylazacycloheptane, 1-(4'-amino-3'-methylphenyl)-2-methylazacycloheptane, 1-(4'-amino-3'-ureidophenyl)-3-hydroxyazacycloheptane, 1-N-4'-hydroxybutyl-1-N-(hydroxyethyloxyethyloxyethyl)-3-isopropyl-para-phenylenediamine, 1-N-methyl-1-N-(hydroxyethyloxyethyloxyethyl)-para-phenylenediamine, 1-N,N-bis(hydroxyethyloxyethyloxyethyl)-para-phenylenediamine, 1-N,N-bis(hydroxyethyloxyethyloxyethyloxyethyl)-3-isopropyl-para-phenylenediamine, 1-N,N-bis(hydroxyethyloxyethyloxyethyloxyethyl)-3-isopropyl-para-phenylenediamine, 1-N,N-bis(hydroxyethyloxyethyloxyethyloxyethyloxyethyloxyethyloxyethyl)-3-methyl-para-phenylenediamine, 1-N,N-bis(benzyloxyethyloxyethyloxyethyl)-3-isopropyl-para-phenylenediamine and their addition salts with an acid.

The para-phenylenediamine derivative or derivatives of formula (I) used as oxidation base in the dyeing composition in accordance with the invention preferably represent from 0.0001 to 20% by weight approximately, more preferably from 0.001 to 15% by weight and more preferably still from 0.01 to 10% by weight with respect to the total weight of the composition.

Mention may more particularly be made, among the meta-aminophenols of above formula (II), of meta-aminophenol, 5-amino-2-methoxyphenol, 5-amino-2-(β- hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol and their addition salts with an acid.

Use will preferably be made, among the substituted meta-diphenols which can be used as couplers in the dyeing composition in accordance with the invention, of the compounds of following formula (III) and their addition salts with an acid:

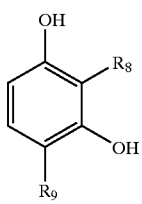
(III)

in which:
R₈ and R₉, which are identical or different, represent a hydrogen atom, a $C_1$–$C_4$ alkyl radical or a halogen atom chosen from chlorine, bromine or fluorine; it being understood that at least one of the R₈ and R₉ radicals is other than a hydrogen atom.

Mention may more particularly be made, among the substituted meta-diphenols of above formula (III), of 2-methyl-1,3-dihydroxybenzene, 4-chloro-1,3-dihydroxybenzene, 2-chloro-1,3-dihydroxybenzene and their addition salts with an acid.

Use will preferably be made, among the substituted meta-phenylenediamines which can be used as couplers in the dyeing composition in accordance with the invention, of the compounds of following formula (IV) and their addition salts with an acid:

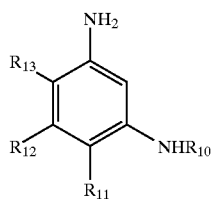
(IV)

in which:
$R_{10}$ represents a hydrogen atom or a $C_1$–$C_4$ alkyl, $C_1$–$C_4$ monohydroxyalkyl or $C_2$–$C_4$ polyhydroxyalkyl radical;

$R_{11}$ and $R_{12}$, which are identical or different, represent a hydrogen atom or a $C_1$–$C_4$ alkyl, $C_1$–$C_4$ monohydroxyalkoxy or $C_2$–$C_4$ polyhydroxyalkoxy radical;

$R_{13}$ represents a hydrogen atom, a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxyalkoxy radical; it being understood that at least one of the $R_{10}$ to $R_{13}$ radicals is other than a hydrogen atom.

Mention may more particularly be made, among the substituted meta-phenylenediamines of above formula (IV), of 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-(methylamino)benzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)-benzene, 2,4-diamino-1-(β-hydroxyethyloxy)benzene, 2-amino-4-N-(β-hydroxyethyl)amino-1-methoxybenzene and their addition salts with an acid.

Mention may in particular be made, among the heterocyclic couplers which can be used in the dyeing composition in accordance with the invention the invention, of indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives and their addition salts with an acid.

Mention is more particularly made, among the indole derivatives which are used as heterocyclic couplers in the dyeing composition in accordance with the invention, of the compounds of following formula (V) and their addition salts with an acid:

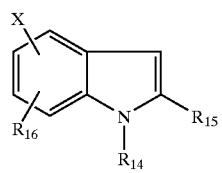
(V)

in which:
$R_{14}$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical, the amine of which is mono- or disubstituted by a $C_1$–$C_4$ alkyl group;

$R_{15}$ represents a hydrogen atom or a $C_1$–$C_4$ alkyl radical;

$R_{16}$ represents a hydrogen atom or a $C_1$–$C_4$ alkyl or hydroxyl radical;

X represents a hydroxyl or $NHR_{17}$ radical in which $R_{17}$ represents a hydrogen atom or a $C_1$–$C_4$ alkyl or $C_1$–$C_4$ hydroxyalkyl radical.

Mention may more particularly be made, among the indole derivatives of above formula (V), of 4-hydroxyindole, 6-hydroxyindole, 7-aminoindole, 6-aminoindole, 7-hydroxyindole, 7-ethyl-6-[(β-hydroxyethyl)amino]indole, 4-aminoindole, 6-hydroxy-1-methylindole, 5,6-dihydroxyindole, 4-hydroxy-1-N-methylindole, 4-hydroxy-2-methylindole, 4-hydroxy-5-methylindole, 4-hydroxy-1-N-(β-hydroxyethyl)indole, 4-hydroxy-1-N-(β-hydroxypropyl)indole, 1-N-(β,γ-dihydroxypropyl)-4-hydroxyindole, 4-hydroxy-1-N-(β-hydroxyethyl)-5-methylindole, 1-N-(γ-dimethylaminopropyl)-4-hydroxyindole and their addition salts with an acid.

Mention may particularly be made, among the indoline derivatives which can be used as heterocyclic couplers in the dyeing composition in accordance with the invention, of 4-hydroxyindoline, 6-hydroxyindoline, 6-aminoindoline, 5,6-dihydroxyindoline and their addition salts with an acid.

Mention may more particularly be made, among the benzimidazole derivatives which can be used as heterocyclic couplers in the dyeing composition in accordance with the invention, of the compounds of following formula (VI) and their addition salts with an acid:

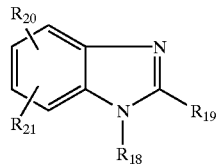

(VI)

in which:
- $R_{18}$ represents a hydrogen atom or a $C_1$–$C_4$ alkyl radical,
- $R_{19}$ represents a hydrogen atom or a $C_1$–$C_4$ alkyl or phenyl radical,
- $R_{20}$ represents a hydroxyl, amino or methoxy radical,
- $R_{21}$ represents a hydrogen atom or a hydroxyl, methoxy or $C_1$–$C_4$ alkyl radical;

with the proviso that:
- when $R_{20}$ denotes an amino radical, then it occupies the 4-position,
- when $R_{20}$ occupies the 4-position, then $R_{21}$ occupies the 7-position,
- when $R_{20}$ occupies the 5-position, then $R_{21}$ occupies the 6-position.

Mention may more particularly be made, among the benzimidazole derivatives of above formula (VI), of 4-hydroxybenzimidazole, 4-aminobenzimidazole, 4-hydroxy-7-methylbenzimidazole; 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-1-methylbenzimidazole, 5,6-dimethoxybenzimidazole and their addition salts with an acid.

Mention may more particularly be made, among the benzomorpholine derivatives which can be used as heterocyclic couplers in the dyeing composition in accordance with the invention, of the compounds of following formula (VII) and their addition salts with an acid:

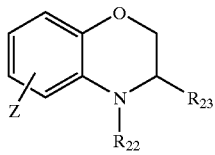

(VII)

in which:
- $R_{22}$ and $R_{23}$, which are identical or different, represent a hydrogen atom or a $C_1$–$C_4$ alkyl radical,
- Z represents a hydroxyl or amino radical.

Mention may more particularly be made, among the benzomorpholine derivatives of above formula (VII), of 6-hydroxy-1,4-benzomorpholine, N-methyl-6-hydroxy-1,4-benzomorpholine, 6-amino-1,4-benzomorpholine and their addition salts with an acid.

Mention may particularly be made, among the sesamol derivatives which can be used as heterocyclic couplers in the dyeing composition in accordance with the invention, of the compounds of following formula (VIII) and their addition salts with an acid:

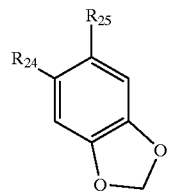

(VIII)

in which:
- $R_{24}$ denotes a hydroxyl, amino, ($C_1$–$C_4$)alkylamino, monohydroxy($C_1$–$C_4$)alkylamino or polyhydroxy ($C_2$–$C_4$) alkylamino radical,
- $R_{25}$ denotes a hydrogen or halogen atom or a $C_1$–$C_4$ alkoxy radical.

Mention may more particularly be made, among the sesamol derivatives of above formula (VIII) of 2-bromo-4,5-methylenedioxyphenol, 2-methoxy-4,5-methylenedioxyaniline, 2-(P-hydroxyethyl)amino-4,5-methylenedioxybenzene and their addition salts with an acid.

Mention may more particularly be made, among the pyrazoloazole derivatives which can be used as heterocyclic couplers in the dyeing composition in accordance with the invention, of the compounds disclosed in the following patent applications and patents: FR-A-2 075 583, EP-A-0 119 860, EP-A-0 285 274, EP-A-0 244 160, EP-A-0 578 248, GB 1 458 377, U.S. Pat. No. 3,227,554, U.S. Pat. No. 3,419,391, U.S. Pat. No. 3,061,432, U.S. Pat. No. 4,500,630, U.S. Pat. No. 3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982 and JP 85/190779, and in the following publications: Chem. Ber., 32, 797 (1899), Chem. Ber., 89, 2550 (1956), J. Chem. Soc. Perkin Trans T., 2047 (1977), J. Prakt. Chem., 320, 533 (1978); the teachings of which form an integral part of the present application.

Mention may very particularly be made, as pyrazoloazole derivatives, of:
- 2-methylpyrazolo[1,5-b]-1,2,4-triazole,
- 2-ethylpyrazolo[1,5-b],2,4-triazole,
- 2-isopropylpyrazolo[1,5-b]-1,2,4-triazole,
- 2-phenylpyrazolo[1,5-b]-1,2,4-triazole,
- 2,6-dimethylpyrazolo[1,5-b]-1,2,4-triazole,
- 7-chloro-2,6-dimethylpyrazolo[1,5-b]-1,2,4-triazole,
- 3,6-dimethylpyrazolo[3,2-c]-1,2,4-triazole,
- 6-phenyl-3-methylthiopyrazolo[3,2-c]-1,2,4-triazole,
- 6-aminopyrazolo[1,5-a]benzimidazole, and their addition salts with an acid.

Mention may more particularly be made, among the pyrroloazole derivatives which can be used as heterocyclic couplers in the dyeing composition in accordance with the invention, of the compounds disclosed in the following patent applications and patents: U.S. Pat. No. 5,256,526, EP-A-0 557 851, EP-A-0 578 248, EP-A-0 518 238, EP-A-0 456 226, EP-A-0 488 909 and EP-A-0 488 248, and in the following publications:
- D. R. Liljegren, Ber., 1964, 3436;
- E. J. Browne, J.C.S., 1962, 5149;
- P. Magnus, J.A.C.S., 1990, 112, 2465;
- P. Magnus, J.A.C.S., 1987, 109, 2711;
- Angew. Chem., 1960, 72, 956; and
- Rec. Trav. Chim., 1961, 80, 1075; the teachings of which form an integral part of the present application.

Mention may very particularly be made, as pyrroloazole derivatives, of:

5-cyano-4-ethoxycarbonyl-8-methylpyrrolo[1,2-b]-1,2,4-triazole, 5-cyano-8-methyl-4-phenylpyrrolo[!,2-b]-1,2,4-triazole, 7-amido-6-ethoxycarbonylpyrrolo[1,2-a]benzimidazole, and their addition salts with an acid.

Mention may more particularly be made, among the imidazoloazole derivatives which can be used as heterocyclic couplers in the dyeing composition in accordance with the invention, of the compounds disclosed in the following patent applications and patents: U.S. Pat. No. 5,441,863; JP 62-279 337; JP 06-236 011 and JP 07-092 632, the teachings of which form an integral part of the present application.

Mention may very particularly be made, as imidazoloazole derivatives, of:

7,8-dicyanoimidazolo[3,2-a]imidazole, 7,8-dicyano-4-methylimidazolo[3,2-a]imidazole, and their addition salts with an acid.

Mention may more particularly be made, among the pyrazolopyrimidine derivatives which can be used as heterocyclic couplers in the dyeing composition in accordance with the invention, of the compounds disclosed in Patent Application EP-A-0 304 001, the teaching of which forms an integral part of the present application.

Mention may very particularly be made, as pyrazolopyrimidine derivatives, of:

pyrazolo[1,5-a]pyrimidin-7-one, 2,5-dimethylpyrazolo[1,5-a]pyrimidin-7-one, 2-methyl-6-ethoxycarbonylpyrazolo[1,5-a]pyrimidin-7-one, 2-methyl-5-(methoxymethyl)pyrazolo[1,5-a]pyrimidin-7-one, 2-tertbutyl-5-trifluoromethylpyrazolo[1,5-a]-pyrimidin-7-one, 2,7-dimethylpyrazolo[1,5-a]pyrimidin-5-one, and their addition salts with an acid.

Mention may more particularly be made, among the pyrazoline-3,5-dione derivatives which can be used as heterocyclic couplers in the dyeing composition in accordance with the invention, of the compounds disclosed in the following patent applications and patents: JP 07-036159, JP 07-084348 and U.S. Pat. No. 4,128,425, and in the following publications:

L. Wyzgowska, Acta. Pol. Pharm., 1982, 39 (1-3), 83

E. Hannig, Pharmazie, 1980, 35 (4), 231

M. H. Elnagdi, Bull. Chem. Soc. Jap., 46 (6), 1830, 1973

G. Cardillo, Gazz. Chim. Ital., 1966, 96 (8-9), 973; the teachings of which form an integral part of the present application.

Mention may very particularly be made, as pyrazoline-3,5-dione derivatives, of:

1,2-diphenylpyrazoline-3,5-dione, 1,2-diethylpyrazoline-3,5-dione, and their addition salts with an acid.

Mention may more particularly be made, among the pyrrolo[3,2-d]oxazole derivatives which can be used as heterocyclic couplers in the dyeing composition in accordance with the invention, of the compounds disclosed in Patent Application JP 07 325 375, the teaching of which forms an integral part of the present application.

Mention may more particularly be made, among the pyrazolo[3,4-d]thiazole derivatives which can be used as heterocyclic couplers in the dyeing composition in accordance with the invention, of the compounds disclosed in Patent Application JP 07 244 361 and in J. Heterocycl. Chem., 16, 13 (1979).

Mention may more particularly be made, among the thiazoloazole S-oxide and thiazoloazole S,S-dioxide derivatives which can be used as heterocyclic couplers in the dyeing composition in accordance with the invention, of the compounds disclosed in the following documents:

JP 07 098489;

Khim. Geterotsilk. Soedin, 1967, p. 93;

J. Prakt. Chem., 318, 1976, p. 12;

Indian J. Heterocycl. Chem., 1995, 5(2), p. 135;

Acta. Pol. Pharm., 1995, 52(5), 415;

Heterocycl. Commun., 1995, 1(4), 297;

Arch. Pharm. (Weinheim, Ger.), 1994, 327(12), 825.

Use will preferably be made, among the naphthols and acylated naphthols which can be used as couplers in the dyeing composition in accordance with the invention, of the compounds of following formula (IX) and their addition salts with an acid:

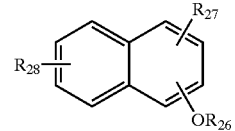

(IX)

in which:

$R_{26}$ represents a hydrogen atom or a —CO—R group in which R represents a $C_1$-$C_4$ alkyl radical;

$R_{27}$ represents a hydrogen atom, a hydroxyl or $C_1$-$C_4$ alkyl radical or an —$SO_3H$ group;

$R_{28}$ represents a hydrogen atom or a hydroxyl radical; it being understood that at least one of the R26 to $R_{28}$ radicals is other than a hydrogen atom.

Mention may in particular be made, among the naphthols and acylated naphthols of formula (IX) which can be used as couplers in the dyeing composition in accordance with the invention, of 1,7-dihydroxynaphthalene, 2,7-dihydroxynaphthalene, 2,5-dihydroxynaphthalene, 2,3-dihydroxynaphthalene, 1-acetoxy-2-methylnaphthalene, 1-hydroxy-2-methylnaphthalene, 1-hydroxy-4-naphthalenesulphonic acid and their addition salts with an acid.

The coupler or couplers as defined above according to the invention preferably represent from 0.0001 to 10% by weight approximately of the total weight of the composition and more preferably still from 0.005 to 5% by weight approximately of this weight.

The dyeing composition in accordance with the invention can, in addition to the coupler or couplers defined above, comprise one or more additional couplers.

These additional couplers are chosen more particularly from 2-methyl-5-aminophenol, 1,3-dihydroxybenzene or 1,3-diaminobenzene.

When they are present, the additional coupler or couplers preferably represent from 0.0001 and 8% by weight with respect to the total weight of the composition.

The dyeing composition in accordance with the invention can moreover include one or more additional oxidation bases other than the substituted para-phenylenediamine derivatives of formula (I) and/or one or more direct dyes.

Mention may be made, among the additional oxidation bases which can be used in the dyeing composition in accordance with the invention, of para-phenylenediamines other than those of formula (I), such as, for example, para-phenylenediamine, para-tolylenediamine, 2-hydroxyethyl-para-phenylenediamine or 1-N,N-bis(β-hydroxyethyl)-para-phenylenediamine, para-aminophenols, such as, for example, 3-methyl-4-aminophenol and 4-aminophenol, ortho-phenylenediamines, ortho-aminophenols, double bases or heterocyclic bases, such as pyrimidines, like, for example, 2,4,5,6-tetraminopyrimidine, or such as pyrazoles, like, for example, 1-(2-hydroxyethyl)-4,5-diaminopyrazole.

When they are present, the additional oxidation base or bases represent from 0.0001 and 15% by weight with respect to the total weight of the dyeing composition.

Generally, the addition salts with an acid which can be used in the context of the dyeing compositions of the invention are chosen in particular from hydrochlorides, hydrobromides, sulphates, tartrates, lactates and acetates.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol; glycerol; glycols and glycol ethers, such as 2-butoxyethanol, propylene glycol, propylene glycol monomethyl ether, diethylene glycol monoethyl ether and diethylene glycol monomethyl ether; and aromatic alcohols such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 12. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, carboxylic acids, such as tartaric acid, citric acid or lactic acid, or sulphonic acids.

Mention may be made, among basifying agents, by way of example, of aqueous ammonia, akaline carbonates, alkanolamines, such as mono-, di- and triethanolamines, and their derivatives, hydroxyalkylamines and ethylenediamines, which are oxyethylenated and/or oxypropylenated, sodium hydroxide, potassium hydroxide and the compounds of following formula(X):

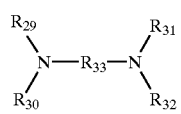

(X)

in which $R_{33}$ is a propylene residue optionally substituted by a hydroxyl group or a $C_1$–$C_4$ alkyl radical and $R_{29}$, $R_{30}$, $R_{31}$ and $R_{32}$, which are identical or different, represent a hydrogen atom or a $C_1$–$C_4$ alkyl or $C_1$–$C_4$ hydroxyalkyl radical.

The dyeing composition in accordance with the invention can also include various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents, reducing or antioxidizing agents, penetration agents, sequestering agents, fragrances, buffers, dispersing agents, conditioning agents, such as, for example, silicones, film-forming agents, preserving agents, opacifying agents, silicone or non-silicone UV screening agents, vitamins or provitamins.

The reducing or antioxidizing agents can be chosen in particular from sodium sulphite, thioglycolic acid, thiolactic acid, sodium bisulphite, dehydro-ascorbic acid, hydroquinone, 2-methylhydroquinone, tert-butylhydroquinone and homogentisic acid and they are then generally present in amounts which can vary between 0.05 and 1.5% by weight approximately with respect to the total weight of the composition.

The dyeing composition in accordance with the invention preferably includes at least one nonionic surface-active agent in a proportion preferably varying between 0.1 and 20% by weight approximately with respect to the total weight of the composition and at least one cationic or amphoteric substantive polymer in proportion preferably varying between 0.05 and 10% by weight with respect to the total weight of the composition.

The dyeing composition in accordance with the invention preferably includes at least one thickening polymer comprising at least one hydrophilic unit and at least one fatty chain in a proportion preferably varying between 0.05 and 10% by weight with respect to the total weight of the composition.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition in accordance with the invention can be provided in various forms, such as in the form of liquids, creams or gels or in any other form appropriate for carrying out dyeing of keratinous fibres and in particular human hair.

Another subject-matter of the invention is a process for the oxidation dyeing of keratinous fibres and in particular human keratinous fibres, such as the hair, employing the dyeing composition as defined above.

According to this process, at least one dyeing composition as defined above is applied to the fibres, the colour being developed at acidic, neutral or alkaline pH using an oxidizing agent which is added only at the time of use to the dyeing composition or which is present in an oxidizing composition applied simultaneously or sequentially in a separate fashion.

According to a particularly preferred embodiment of the dyeing process according to the invention, the dyeing composition as defined above is mixed, at the time of use, with an oxidizing composition comprising, in a medium appropriate for dyeing, at least one oxidizing agent present in an amount sufficient to develop a colouring. The mixture obtained is subsequently applied to the keratinous fibres and is left to stand for 3 to 50 minutes approximately, preferably 5 to 30 minutes approximately, after which the hair is rinsed, washed with shampoo, rinsed again and dried.

The oxidizing agent can be chosen from oxidizing agents conventionally used for the oxidation dyeing of keratinous fibres and among which may be mentioned hydrogen peroxide, urea hydrogen peroxide, alkali metal bromates, persalts, such as perborates and persulphates, peracids and oxidation enzymes, such as peroxidases, laccases, tyrosinases and oxidoreductases, among which may in particular be mentioned pyranose oxidases, glucose oxidases, glycerol oxidases, lactate oxidases, pyruvate oxidases and uricases, the said enzymes optionally being used in combination with their respective donors.

The pH of the oxidizing composition including the oxidizing agent as defined above is such that, after mixing with the dye composition, the pH of the resulting composition applied to keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels or in any other form appropriate for carrying out dyeing of keratinous fibres and in particular of human hair.

Another subject-matter of the present invention is a multi-compartment device or multi-compartment dyeing kit or any other packaging system with several compartments, a first compartment of which includes the dyeing composition as defined above and a second compartment of which includes the oxidizing composition as defined above. These devices can be. equipped with a means allowing the desired mixture to be delivered to the hair, such as the devices disclosed in Patent FR-2 586 913 on behalf of the Applicant Company.

The examples which follow are intended to illustrate the invention.

DYEING EXAMPLES 1 TO 4

The following dyeing compositions in accordance with the invention were prepared:

| EXAMPLES | 1 | 2 | 3 | 4 |
|---|---|---|---|---|
| 1-(4'-Amino-3'-methylphenyl)-4-hydroxy-2-methylpyrrolidine dihydrochloride (substituted para-phenylenediamine derivative of formula (I) in accordance with the invention) | $3 \times 10^{-3}$ mol | $3 \times 10^{-3}$ mol | $3 \times 10^{-3}$ mol | $3 \times 10^{-3}$ mol |
| 2,4-Diamino-1-(β-hydroxyethyloxy)-benzene dihydrochloride (coupler) | $3 \times 10^{-3}$ mol | — | — | — |
| 2-Methyl-1,3-dihydroxy-benzene (coupler) | — | $3 \times 10^{-3}$ mol | — | — |
| 4-Hydroxyindole (coupler) | — | — | $3 \times 10^{-3}$ mol | — |
| 1-Naphthol | — | — | — | $3 \times 10^{-3}$ mol |
| Common dyeing vehicle | (*) | (*) | (*) | (*) |
| Demineralized water, q.s. for | 100 g | 100 g | 100 g | 100 g |

| (*) Common dyeing vehicle: | |
|---|---|
| $C_8$–$C_{10}$ Alkyl polyglucoside as a 60% aqueous solution, sold under the name Oramix CG 110 ® by Seppic | 5.4 g |
| Ethanol | 18.0 g |
| Benzyl alcohol | 1.8 g |
| Polyethylene glycol 400 | 2.7 g |
| Pentasodium salt of diethylenetriaminepentaacetic acid as a 40% aqueous solution, sold under the name Dissoluine D-40 ® by Akzo | 1.08 g |
| Sodium metabisulphite | 0.205 g |
| Aqueous ammonia comprising 20.5% of $NH_3$ | 10.0 g |

At the time of use, the dyeing compositions described above were mixed, weight for weight, with a 20-volume hydrogen peroxide solution (6% by weight).

The mixtures thus prepared were applied for 30 minutes to locks of permed natural grey hair comprising 90% of white hairs. The locks were subsequently rinsed, washed with a standard shampoo, rinsed again and then dried.

The hair samples were dyed in the following shades:

| EXAMPLES | Shades obtained |
|---|---|
| 1 | Strong blue |
| 2 | Strong golden |
| 3 | Strong golden coppery |
| 4 | Strong blue-grey |

What is claimed is:

1. A composition comprising at least one oxidation base and at least one coupler, wherein:
   (A) said at least one oxidation base is chosen from compounds of formula (I), and acid addition salts thereof:

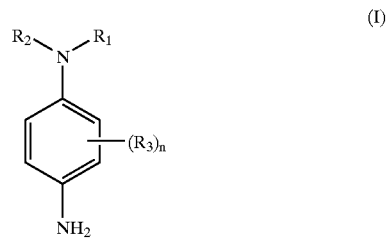

wherein
(a) $R_1$ and $R_2$, together with the nitrogen atom to which they are attached, form a saturated 5-, 6-, or 7-membered heterocycle, wherein said heterocycle may be substituted by at least one substituent containing at least one atom chosen from carbon, nitrogen, oxygen and sulphur;
(b) $R_3$ is chosen from halogen atoms, alkyl groups, aryl groups, heterocycles, cyano groups, nitro groups, hydroxyl groups, carboxyl groups, sulpho groups, alkoxy groups, aryloxy groups, cyanoamino groups, amino groups, anilino groups, ureido groups, sulphamoyl groups, mono- or dialkyl-sulphamylamino groups, alkylthio groups, arylthio groups, alkoxycarbonylamino groups, sulphonamido groups, carbamyl groups, mono- or dialkylcarbamylsulphamyl groups, alkylsulphonyl groups, alkoxycarbonyl groups, azo groups, acyloxy groups, carbamyloxy groups, monoalkylcarbamyloxy groups, dialkylcarbamyloxy groups, silyl groups, silyloxy groups, aryloxycarbonylamino groups, imido groups, sulphinyl groups, phosphonyl groups, aryloxycarbonyl groups, acyl groups, and mercapto groups;
wherein said alkyl groups contain from 1 to 25 carbon atoms, are linear, branched, or cyclic, and are substituted by one or more groups chosen from monohydroxyalkyl groups, polyhydroxyalkyl groups, alkoxyalkyl groups, and aminoalkyl groups optionally substituted with one or more groups chosen from carboxyalkyl groups, alkylcarboxyalkyl groups, thioalkyl groups, alkylthioalkyl groups, cyanoalkyl groups, trifluoroalkyl groups, sulphoalkyl groups, phosphoalkyl groups, and haloalkyl groups;
wherein said alkoxy groups contain from 1 to 25 carbon atoms and are linear, branched, or cyclic;

wherein said aryl groups contain from 6 to 26 carbon atoms and may be substituted by one or more groups chosen from alkyl groups, substituted alkyl groups, and alkoxy groups; and wherein said heterocycles are chosen from monocyclic and polycyclic heterocylces, each comprising 3, 4, 5, or 6 ring members containing one or more heteroatoms, wherein, in the case of polycyclic heterocycles, at least one of the rings contains at least one heteroatom chosen from nitrogen, oxygen, and sulfur; and (c) n is an integer ranging from 0 to 4, wherein when n is greater than 1, then the $R_3$ groups may be identical or different and together may optionally form a saturated or unsaturated 3-, 4-, 5-, or 6-membered ring;

with the proviso that:

1) the compounds of formula (I) do not contain more than 3 hydroxyl groups;

2) when $R_1$ and $R_2$ form a pyrrolidine ring substituted by a carbamoyl radical on the carbon in the position α to the nitrogen atom to which they are attached, then n is not 0; or if n is 0, then the pyrrolidine ring carries at least two substituents;

3) when $R_1$ and $R_2$ form a pyrrolidine ring substituted by a hydroxymethyl group on the carbon situated in the α position with respect to the nitrogen atom to which they are attached, and when n is 0 or 1, then either the said pyrrolidine ring contains at least two additional substituents or the said pyrrolidine ring contains only one additional substituent other than a hydroxyl radical on the carbon situated in the β position With respect to the nitrogen atom and with respect to the carbon carrying the said hydroxymethyl substituent; and when n is 1, then $R_3$ is not chosen from alkyl groups, monohydroxyalkyl groups, or polyhydroxyalkyl groups; and $R_1$ and $R_2$ form a heterocycle other than a piperazine or diazacyoloheptane; and (B) said at least one coupler is chosen from heterocyclic couplers, substituted meta-diphenols, substituted meta-phenylenediamines, naphthols, acylated naphthols, meta-aminophenols of formula (II), and acid addition salts thereof:

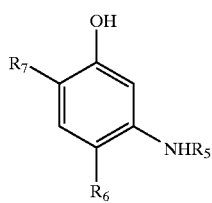

(II)

wherein:

$R_5$ is chosen from hydrogen, $C_1$–$C_4$ alkyl groups, $C_1$–$C_4$ monohydroxyalkyl groups, and $C_2$–$C_4$ polyhydroxyalkyl groups;

$R_6$ is chosen from hydrogen, $C_1$–$C_4$ alkyl groups, $C_1$–$C_4$ alkoxy groups, chlorine, bromine, and fluorine;

$R_7$ is chosen from hydrogen, $C_1$–$C_4$ alkyl groups, $C_1$–$C_4$ alkoxy groups, $C_1$–$C_4$ monohydroxyalkyl groups, $C_1$–$C_4$ polyhydroxyalkyl groups, $C_1$–$C_4$ monohydroxyalkoxy groups, and $C_1$–$C_4$ polyhydroxyalkoxy groups;

with the proviso that, when $R_7$ is chosen from methyl and $R_6$ is chosen from hydrogen, then $R_5$ is not chosen from hydrogen.

2. A composition according to claim 1, wherein said at least one oxidation base is chosen from compounds of formula (I) and acid addition salts thereof, wherein:

a) $R_1$ and $R_2$, together with the nitrogen atom to which they are attached, form a saturated 5-, 6-, or 7-membered heterocycle, wherein said heterocycle may be substituted by at least one substituent containing at least one atom chosen from carbon, nitrogen, and oxygen, wherein said at least one atom is not situated in the meta position with respect to the nitrogen atom of the heterocycle;

(b) $R_3$ is chosen from halogen, alkyl groups, aryl groups, and heterocycles; and (c) n ranges from 0 to 2.

3. A composition according to claim 1, wherein said at least one oxidation base is chosen from 1-(4'-amino-3'-isopropyloxy-phenyl)-2,6-dimethylpyrrolidine, 1-(4'-amino-3'-methylphenyl)-3-(hydroxyethyloxy)pyrrolidine, 1-(4'-amino-3'-methylphenyl)-4-hydroxy-2-methylpyrrolidine, 1-(4'-amino-3'-methylphenyl)-3-(methylsulphonamido)pyrrolidine, 1-(4'-amino-3'-phenoxyphenyl)-3-(methylsulphonamido)pyrrolidine, 3-n-butylpyrrolidine-1-(4'-amino-3'-phenylsulphonic acid), 1-(4'-amino-3'-acetylaminophenyl)-3-(hydroxymethyl) pyrrolidine, 7-amino-4-(2'-methyl)-pyrrolydinyl-benzofuran, 1-(4'-aminophenyl)-2-(4"-aminophenoxymethyl)piperidine, 1-(4'-amino-3'-acetylphenyl)-4-hydroxypiperidine, 1-(4'-aminophenyl)-2-(hydroxyethyl)piperidifne, 1-(4'-amino-3'-methoxyphenyl)-2,6-di(hydroxymethyl)piperidine, 1-(4'-amino-3'-isopropyloxyphenyl)-2,6-dimethyl-piperidine, 1-(4'-amino-3'-isopropylphenyl)-2-(hydroxymethyl)piperidine, 1-(4'-amino-3'-isopropyloxyphenyl)-2-(hydroxymethyl)piperidine, 1-(4'-amino-3'-aminophenyl)-2-(hydroxymethyl)piperidine, 1-(4'-amino-3'-dimethylaminophenyl)-2-(mercaptoethyloxyethyl)piperidine, 1-(4'-amino-3'(2'",4'"-dichloro)anilinophenyl)-4-methylpiperidine, 1-(4'-aminophenyl)-4-methylpiperidine, 1-(4'-aminophenyl)-2,7-dimethylazacycloheptane, 1-(4'-amino-3'-methylphenyl)-2-methylazacycloheptane, 1-(4'-amino-3'-ureidophenyl)-3-hydroxyazacycloheptane, 1-(4'-amino-3'-sulphamoylaminophenyl)-2,7-dimethylazacycloheptane, 1-(4'-amino-3'-methylthiophenyl)-2,7-dimethylazacycloheptane, and acid addition salts thereof.

4. A composition according to claim 3, wherein said at least one oxidation base is chosen from 1-(4'-amino-3'-methylphenyl)-3-(hydroxyethyloxy)pyrrolidine, 1-(4'-amino-3'-methylphenyl)-4-hydroxy-2-methylpyrrolidine, 1-(4'-amino-3'-methylphenyl)-3-(methylsulphonamido) pyrrolidine, 1-(4'-amino-3'-phenoxyphenyl)-3-(methylsulphonamido)pyrrolidine, 1-(4'-aminophenyl)-2-(4"-aminophenoxymethyl)piperidine, 1-(4'-aminophenyl)-2-(hydroxyethyl)piperidine, 1-(4'-amino-3'-isopropylphenyl)-2-(hydroxymethyl)piperidine, 1-(4'-aminophenyl)-4-methylpiperidine, 1-(4'-aminophenyl)-2,7-dimethylazacycloheptane, 1-(4'-amino-3'-methylphenyl)-2-methylazacycloheptane, 1-(4'-amino-3'-ureidophenyl)-3-hydroxyazacycloheptane, and acid addition salts thereof.

5. A composition according to claim 1, wherein said at least one oxidation base is present in an amount ranging from about 0.0001% to about 20%, by weight, relative to the total weight of the composition.

6. A composition according to claim 1, wherein $R_1$ and $R_2$ form a pyrrolidine ring.

7. A composition according to claim 1, wherein said at least one coupler is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid addition salts thereof.

8. A composition according to claim 1, wherein said at least one coupler is chosen from compounds of formula (III), and acid addition salts thereof:

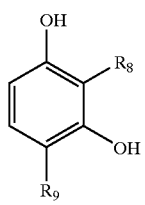

(III)

wherein:
$R_8$ and $R_9$, which may be the same or different, are each chosen from hydrogen, $C_1$–$C_4$ alkyl groups, chlorine, bromine, and fluorine; with the proviso that at least one of $R_8$ and $R_9$ is not hydrogen.

9. A composition according to claim 8, wherein said at least one coupler is chosen from 2-methyl-1,3-dihydroxybenzene, 4-chloro-1,3-dihydroxybenzene, 2-chloro-1,3-dihydroxybenzene, and acid addition salts thereof.

10. A composition according to claim 1, wherein said at least one coupler is chosen from compounds of formula (IV), and acid addition salts thereof:

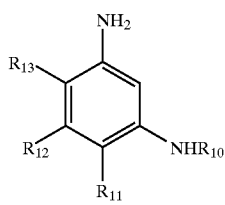

(IV)

wherein:
$R_{10}$ is chosen from hydrogen, $C_1$–$C_4$ alkyl groups, $C_1$–$C_4$ monohydroxyalkyl groups, and $C_2$–$C_4$ polyhydroxyalkyl groups;

$R_{11}$ and $R_{12}$, which may be the same or different, are each chosen from hydrogen, $C_1$–$C_4$ alkyl groups, $C_1$–$C_4$ monohydroxyalkoxy groups, and $C_2$–$C_4$ polyhydroxyalkoxy groups; and $R_{13}$ is chosen from hydrogen, $C_1$–$C_4$ alkoxy groups, $C_1$–$C_4$ aminoalkoxy groups, $C_1$–$C_4$ monohydroxyalkoxy groups, $C_2$–$C_4$ polyhydroxyalkoxy groups, and 2,4-diaminophenoxyalkoxy groups;

with the proviso that at least one of $R_{10}$, $R_{11}$, $R_{12}$, and $R_{13}$ is not hydrogen.

11. A composition according to claim 10, wherein said at least one coupler is chosen from 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-(methylamino)benzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene, 2-amino-4-N-(β-hydroxyethyl)amino-1-methoxybenzene, and acid addition salts thereof.

12. A composition according to claim 1, wherein said at least one heterocylic coupler is chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and acid addition salts thereof.

13. A composition according to claim 12, wherein said indole derivatives are chosen from compounds of formula (V), and acid addition salts thereof:

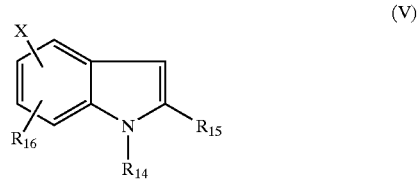

(V)

wherein:

$R_{14}$ is chosen from hydrogen, $C_1$–$C_4$ alkyl groups, $C_1$–$C_4$ monohydroxyalkyl groups, $C_2$–$C_4$ polyhydroxyalkyl groups, and $C_1$–$C_4$ aminoalkyl groups wherein the amine is mono- or disubstituted by $C_1$–$C_4$ alkyl groups;

$R_{15}$ is chosen from hydrogen and $C_1$–$C_4$ alkyl groups;

$R_{16}$ is chosen from hydrogen, $C_1$–$C_4$ alkyl groups, and hydroxyl groups; and X is chosen from hydroxyl groups and $NHR_{17}$, wherein $R_{17}$ is chosen from hydrogen, $C_1$–$C_4$ alkyl groups, and $C_1$–$C_4$ hydroxyalkyl groups.

14. A composition according to claim 13, wherein said indole derivatives are chosen from 4-hydroxyindole, 6-hydroxyindole, 7-aminoindole, 6-aminoindole, 7-hydroxyindole, 7-ethyl-6-[(β-hydroxyethyl)amino]indole, 4-aminoindole, 6-hydroxy-1-methylindole, 5,6-dihydroxyindole, 4-hydroxy-1-N-methylindole, 4-hydroxy-2-methylindole, 4-hydroxy-5-methylindole, 4-hydroxy-1-N-(β-hydroxyethyl)indole, 4-hydroxy-1-N-(β-hydroxypropyl)indole, 1-N-(β,γ-dihydroxypropyl)-4-hydroxyindole, 4-hydroxy-1-N-(β-hydroxyethyl)-5-methylindole, 1-N-(γ-dimethylaminopropyl)-4-hydroxyindole, and acid addition salts thereof.

15. A composition according to claim 12, wherein said indoline derivatives are chosen from 4-hydroxyindoline, 6-hydroxyindoline, 6-aminoindoline, 5,6-dihydroxyindoline, and acid addition salts thereof.

16. A composition according to claim 12, wherein said benzimidazole derivatives are chosen from compounds of formula (VI), and acid addition salts thereof:

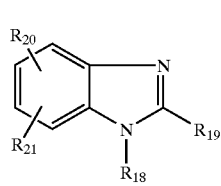

(VI)

wherein:

$R_{18}$ is chosen from hydrogen and $C_1$–$C_4$ alkyl groups;

$R_{19}$ is chosen from hydrogen, $C_1$–$C_4$ alkyl groups, and phenyl groups;

$R_{20}$ is chosen from hydroxyl groups, amino groups, and methoxy groups; and $R_{21}$ is chosen from hydrogen, hydroxyl groups, methoxy groups, and $C_1$–$C_4$ alkyl groups;

with the proviso that:

i) when $R_{20}$ is chosen from amino groups, it occupies the 4-position;

ii) when $R_{20}$ occupies the 4-position, then $R_{21}$ occupies the 7-position; and iii) when $R_{20}$ occupies the 5-position, then $R_{21}$ occupies the 6-position.

17. A composition according to claim 16, wherein said benzimidazole derivatives are chosen from 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole, 5,6-dimethoxybenzimidazole, and acid addition salts thereof.

18. A composition according to claim 12, wherein said benzomorpholine derivatives are chosen from compounds of formula (VII), and acid addition salts thereof:

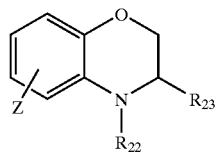

(VII)

wherein:

$R_{22}$ and $R_{23}$, which may be the same or different, are each chosen from hydrogen and $C_1$–$C_4$ alkyl groups; and Z is chosen from hydroxyl groups and amino groups.

19. A composition according to claim 18, wherein said benzomorpholine derivatives are chosen from 6-hydroxy-1,4-benzomorpholine, N-methyl-6-hydroxy-1,4-benzomorpholine, 6-amino-1,4-benzomorpholine, and acid addition salts thereof.

20. A composition according to claim 12, wherein said sesamol derivatives are chosen from compounds of formula (VIII), and acid addition salts thereof:

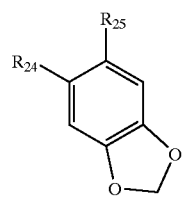

(VIII)

wherein:

$R_{24}$ is chosen from hydroxyl groups, amino groups, $(C_1$–$C_4)$alkylamino groups, monohydroxy$(C_1$–$C_4)$ alkylamino groups, and polyhydroxy$(C_2$–$C_4)$ alkylamino groups; and $R_{25}$ is chosen from hydrogen, halogen atoms, and $C_1$–$C_4$ alkoxy groups.

21. A composition according to claim 20, wherein said sesamol derivatives are chosen from 2-bromo-4,5-methylenedioxyphenol, 2-methoxy-4,5-methylenedioxyaniline, 2-(β-hydroxyethyl)amino-4,5-methylenedioxybenzene, and acid addition salts thereof.

22. A composition according to claim 12, wherein said pyrazoloazole derivatives are chosen from 2-methylpyrazolo[1,5-b]-1,2,4-triazole, 2-ethylpyrazolo[1,5-b]-1,2,4-triazole, 2-isopropylpyrazolo[1,5-b]-1,2,4-triazole, 2-phenylpyrazolo[1,5-b]-1,2,4-triazole, 2,6-dimethylpyrazolo[1,5-b]-1,2,4-triazole, 7-chloro-2,6-dimethylpyrazolo[1,5-b]-1,2,4-triazole, 3,6-dimethylpyrazolo[3,2-c]-1,2,4-triazole, 6-phenyl-3-methylthiopyrazolo[3,2-c]-1,2,4-triazole, 6-aminopyrazolo [1,5-a]benzimidazole, and acid addition salts thereof.

23. A composition according to claim 12, wherein said pyrroloazole derivatives are chosen from 5-cyano-4-ethoxycarbonyl-8-methylpyrrolo[1,2-b]-1,2,4-triazole, 5-cyano-8-methyl-4-phenylpyrrolo[1,2-b]-1,2,4-triazole, 7-amido-6-ethoxycarbonylpyrrolo[1,2-a]benzimidazole, and acid addition salts thereof.

24. A composition according to claim 12, wherein said imidazoloazole derivatives are chosen from 7,8-dicyanoimidazolo[3,2-a]imidazole, 7,8-dicyano-4-methylimidazolo[3,2-a]imidazole, and acid addition salts thereof.

25. A composition according to claim 12, wherein said pyrazolopyrimidine derivatives are chosen from pyrazolo[1,5-a]pyrimidin-7-one, 2,5-dimethylpyrazolo[1,5-a]pyrimidin-7-one, 2-methyl-6-ethoxycarbonylpyrazolo[1,5-a]pyrimidin-7one, 2-methyl-5-(methoxymethyl)pyrazolo[1,5-a]pyrimidin-7-one, 2-tertbutyl-5-trifluoromethylpyrazolo [1,5-a]pyrimidin-7-one, 2,7-dimethylpyrazolo[1,5-a] pyrimidin-5-one, and acid addition salts thereof.

26. A composition according to claim 12, wherein said pyrazoline-3,5-dione derivatives are chosen from 1,2-diphenylpyrazoline-3,5-dione, 1,2-diethylpyrazoline-3,5-dione, and acid addition salts thereof.

27. A composition according to claim 1, wherein said naphthols and acylated naphthols are chosen from compounds of formula (IX), and acid addition salts thereof:

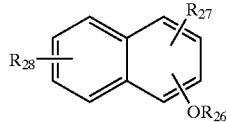

wherein:
- $R_{26}$ is chosen from hydrogen and —CO—R, wherein R is chosen from $C_1$–$C_4$ alkyl groups;
- $R_{27}$ is chosen from hydrogen, hydroxyl groups, $C_1$–$C_4$ alkyl groups, and —SO$_3$H; and
- $R_{28}$ is chosen from hydrogen and hydroxyl groups;

with the proviso that at least one of $R_{26}$, $R_{27}$, and $R_{28}$ is not hydrogen.

28. A composition according to claim 27, wherein said naphthols and acylated naphthols are chosen from 1,7-dihydroxynaphthalene, 2,7-dihydroxynaphthalene, 2,5-dihydroxynaphthalene, 2,3-dihydroxynaphthalene, 1-acetoxy-2-methylnaphthalene, 1-hydroxy-2-methylnaphthalene, 1-hydroxy-4-naphthalenesulphonic acid, and acid addition salts thereof.

29. A composition according to claim 1, wherein said coupler is present in an amount ranging from about 0.0001% to about 10%, by weight, relative to the total weight of said composition.

30. A composition according to claim 1, further comprising at least one additional coupler.

31. A composition according to claim 30, wherein said at least one additional coupler is chosen from 2-methyl-5-aminophenol, 1,3-dihydroxybenzene, and 1,3-diaminobenzene.

32. A composition according to claim 1, further comprising at least one additional oxidation base.

33. A composition according to claim 32, wherein said at least one additional oxidation base is chosen from para-phenylenediamines other than those of formula (I), para-aminophenols, ortho-phenylenediamines, ortho-aminophenols, double bases, and heterocyclic bases.

34. A composition according to claim 1, further comprising, at least one optional ingredient chosen from anionic surfactants, cationic surfactants, non-ionic surfactants, amphoteric surfactants, zwitterionic surfactants, anionic polymers, cationic polymers, non-ionic polymers, amphoteric polymers, zwitterionic polymers, thickeners, reducing agents, antioxidizing agents, penetration agents, sequestering agents, fragrances, buffers, dispersing agents, conditioning agents, film-forming agents, preserving agents, opacifying agents, UV-screening agents, vitamins, and provitamins.

35. A process for the oxidation dyeing of keratinous fibres comprising applying at least one composition according to claim 1 and at least one oxidizing agent to said keratinous fibres at an acidic, neutral, or basic pH.

36. A process according to claim 35, wherein said at least one oxidizing agent is chosen from hydrogen peroxide, urea hydrogen peroxide, alkali metal bromates, persalts, peracids, and oxidation enzymes.

37. A process according to claim 35, wherein said keratinous fibres are human keratinous fibers.

* * * * *